US012338216B2

(12) United States Patent
Giessler-Geiss et al.

(10) Patent No.: US 12,338,216 B2
(45) Date of Patent: Jun. 24, 2025

(54) SOLVATES OF ABSCISIC ACID AND LIQUID COMPOSITIONS CONTAINING ABSCISIC ACID

(71) Applicant: Clariant International Ltd., Muttenz (CH)

(72) Inventors: Stephanie Giessler-Geiss, Frankfurt am Main (DE); Peter Baur, Schondorf (DE); Roland Arnold, Elbtal (DE); Jennifer Neckermann, Selters (DE); Siegfried Staiger, Frankfurt am Main (DE); Luri Stefano Negrisiolo Dario, Frankfurt am Main (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 646 days.

(21) Appl. No.: 17/777,558

(22) PCT Filed: Oct. 28, 2020

(86) PCT No.: PCT/EP2020/080264
§ 371 (c)(1),
(2) Date: May 17, 2022

(87) PCT Pub. No.: WO2021/099079
PCT Pub. Date: May 27, 2021

(65) Prior Publication Data
US 2022/0411370 A1 Dec. 29, 2022

(30) Foreign Application Priority Data
Nov. 19, 2019 (EP) .................................... 19210021

(51) Int. Cl.
C07D 207/267 (2006.01)
A01N 25/06 (2006.01)
A01N 43/36 (2006.01)

(52) U.S. Cl.
CPC ......... *C07D 207/267* (2013.01); *A01N 25/06* (2013.01); *A01N 43/36* (2013.01)

(58) Field of Classification Search
CPC ..... C07D 207/267; A01N 25/06; A01N 43/36
See application file for complete search history.

(56) References Cited

U.S. PATENT DOCUMENTS

| 4,209,530 A | 6/1980 | Visscher |
| 4,434,180 A | 2/1984 | Visscher |
| 5,160,528 A | 11/1992 | Chaudhuri |
| 5,389,688 A | 2/1995 | Narayanan |
| 6,004,905 A | 12/1999 | Abrams |
| 8,278,480 B2 | 10/2012 | Belkind |
| 2020/0323206 A1* | 10/2020 | Aponte ................ A01N 43/653 |

FOREIGN PATENT DOCUMENTS

| EP | 0466353 A1 | 1/1992 |
| JP | H03157305 A | 7/1991 |
| JP | H0459704 A | 2/1992 |
| JP | H0459704 B2 | 9/1992 |
| JP | H07223917 A | 8/1995 |
| JP | 2006151881 A | 6/2006 |
| JP | 2010516811 A | 5/2010 |
| JP | 2019525895 A | 9/2019 |
| WO | 2005104844 A1 | 11/2005 |
| WO | 2008094558 A2 | 8/2008 |
| WO | 2017211572 A1 | 12/2017 |
| WO | 2018143140 A1 | 8/2018 |

OTHER PUBLICATIONS

B.V. Milborrow, "The chemistry and physiology of abscisic acid", Annu. Rev. Plant Physiol. 25: 259-307, 1974, 1 page.
Baur_Pesticide Science 51_131-152, Feb. 8, 2022.
Blumenfeld et al., "Cuticular Penetration of Abscisic Acid", Planta (Berl.) 107, 261-268 (1972).
Bruzzone et al., "The plant hormone abscisic acid increases in human plasma after hyperglycemia and stimulates glucose consumption by adipocytes and myoblasts", Faseb J. 26, 1251-1260 (2012).
Finkelstein et al., "Abscisic Acid Biosynthesis and Response", The Arabidopsis Book, 2002, 49 pages.
Harry G. Brittain, "Theory and Principles of Polymorphic Systems", 3 pages, Feb. 8, 2022.
Hartung et al., "Tansley Review No. 35, Physicochemical properties of plant growth regulators and plant tissues determine their distribution and redistribution: stomatal regulation by abscisic acid in leaves", New Phytol. (1991), 119, 361-382.
Hilfiker et al., "Polymorphism in the Pharmaceutical Industry, Solid form and drug development", Wiley-VCH, 2019, 8 pages.
Hilkert, "Solid State and Polymorphism of the Drug Substance in the Context of QbD", p. 2, Feb. 8, 2022.
Kamuro, "Chemical Regulation of Plants", 11 pages, 1994.
Mauseth Botany, "Chp. 14: Development and morphogenesis", pp. 348-380, 1991.
Peter Baur, "Mechanistic aspect of foliar penetration of agrochemicals and the effect of adjuvants", Recent Res. Develop. Agric. & Food Chemistry, 2, 809-837 (1998).
Raven et al., "Biology of Plants: Fifth Edition", Worth Publishers, Copyright 1971, 1976, 1981, 1986, and 1992, 31 pages.
Richard N. Arteca, "Plant Growth Substances, Principles and Applications", DOI: 10.1007/978-1-4757-2451-6, Springer Science+Business Media Dordrecht, 1996, 347 pages.
Schonherr et al., "Modelling Penetration of Plant Cuticles by Crop Protection Agents and Effects of Adjuvants on their Rates of Penetration", Pestic. Sci. 1994, 42, 185-208.
Taiz, Plant Physiology and Development, 2015, 10 pages.
Zeevaart et al., "Metabolism and Physiology of Abscisic Acid", Ann. Rev. Plant Physiol. Plant Mol. Biol. 1988, 39, 439-473.

(Continued)

*Primary Examiner* — Kamal A Saeed (57) ABSTRACT

The invention relates to new modifications of abscisic acid, to liquid compositions of abscisic acid and to their use in agrochemical applications. The modifications and compositions of the invention contain abscisic acid in the form of a solvate with at least one N-alkyl pyrrolidone, wherein the N-alkyl group has 3 to 6 carbon atoms. These solvates enable formulations with high concentrations of abscisic acid.

19 Claims, 1 Drawing Sheet

(56) References Cited

OTHER PUBLICATIONS

Mauseth, James D. Botany: an introduction to plant biology. Chapter 14, Jones & Bartlett Publishers, 2014, 33 pages.

* cited by examiner

Figure 1:
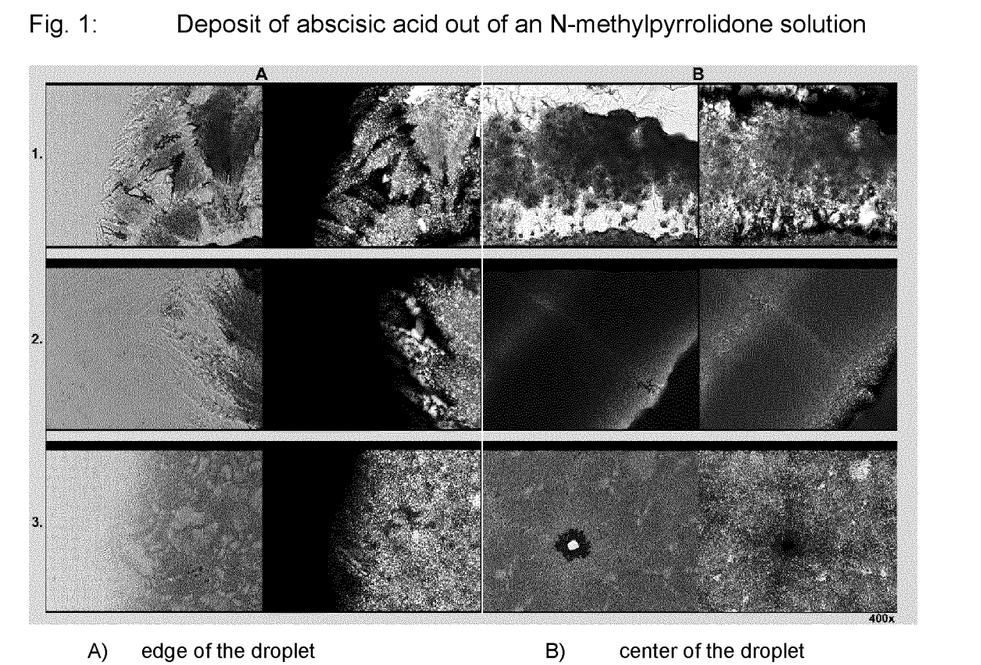

Fig. 1: Deposit of abscisic acid out of an N-methylpyrrolidone solution

A) edge of the droplet      B) center of the droplet

Figure 2:
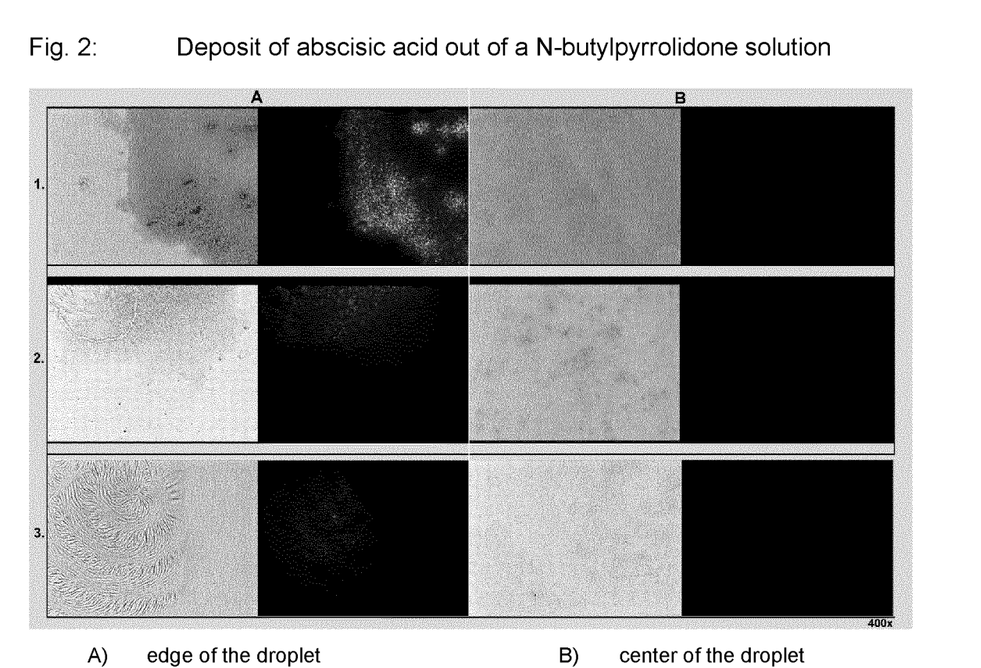

Fig. 2: Deposit of abscisic acid out of a N-butylpyrrolidone solution

A) edge of the droplet      B) center of the droplet

SOLVATES OF ABSCISIC ACID AND LIQUID COMPOSITIONS CONTAINING ABSCISIC ACID

The invention relates to new modifications of abscisic acid. The invention further relates to high load liquid compositions of abscisic acid.

Abscisic acid ("ABA") is a naturally occurring plant hormone, which affects all stages of higher plant growth (Taiz et al. (2015) Plant Physiology and Development. Sinauer Associates; Bruzzone et al. (2012)). It occurs also in mosses, fungi and metazoans and a role of ABA in human beings is discussed. Essential plant growth processes that can be affected include controlling seed development, maturation and germination, maintaining dormancy of buds, acceleration of fruit ripening, activation of the pathogen resistance response defense, induction senescence in already-damaged cells and their proximate neighbors, and support of the plant in tolerating stressful conditions, particularly the lack of sufficient water. (Taiz et al. (2015) Plant Physiology and Development. Sinauer Associates; Arteca, R. (1996), Plant Growth Substances: Principles and Applications. New York: Chapman & Hall; Mauseth, J. D. (1991), Botany: An Introduction to Plant Biology. Philadelphia: Saunders. pp. 348-415; Raven, P. H., Evert, R. F., and Eichhorn, S. E. (1992), Biology of Plants. New York: Worth, pp. 545-572).

Abscisic acid owes its name to the belief that this plant growth regulator causes directly the abscission of leaves from deciduous trees in the fall, which was later found to be valid only in a minority of plant species. Abscisin and dorm in are names previously used for this plant hormone. The chemistry and physiology of abscisic acid and its analogs is described e.g. by Milborrow, Ann. Rev. Plant Physiol. 1974, 25, 259-307. Abscisic acid can act directly as single plant hormone, as in the control of stomatal aperture, or via the balance or induction of other plant hormones like gibberellic acid or ethylene. (Taiz et al. (2015)).

The naturally occurring enantiomeric form of abscisic acid is (S)-(+)-abscisic acid. In some literature reports the (R)-(−)-abscisic acid enantiomer is seen to be biologically inactive. However other research suggests that (R)-(−)-abscisic acid also has some biological activities, yet often different from those of the (S)-(+)-enantiomer (Zeevart J. A. D. and Creelman, R. A. (1988) Metabolism and Physiology of Abscisic Acid, Annu. Rev. Plant Physiol. Plant Mol. Biol. 39, 439-473).

Abscisic acid is a carboxylic acid, and thus in a medium having an acidic pH, it is protonated and in its neutral undissociated form. This uncharged, undissociated form is more lipophilic than a salt of abscisic acid, and penetration of the uncharged acid form into the plant cuticle is favored relative to the charged, dissociated form of abscisic acid present at higher pH (Blumenfeld and Bukovac 1972, Planta 107: 261-268; Schönherr and Baur (1994), Baur (1998)). The uncharged, undissociated form of abscisic acid also crosses cell membranes from the apoplast into the cytosol more easily than a salt form leading to enhanced uptake and superior biological activity. Once in the cell, abscisic acid is dissociated and this ion trap mechanism allows also long distance transport of abscisic acid in the phloem (Hartung and Slovik 1991).

Abscisic acid was first defined in the early 1960s as a growth inhibitor accumulating in abscising cotton fruit and in leaves of sycamore trees photoperiodically induced to become dormant (Finkelstein RR. Rock CD (2002), Abscisic Acid Biosynthesis and Response, The Arabidopsis Book: Vol. 45, No. 1 pp. 1-48). Since then, abscisic acid has been shown to regulate many aspects of plant growth and development, including embryo maturation, seed dormancy, germination, cell division and elongation, etc. Although abscisic acid has historically been thought of as a growth inhibitor, young tissues have high abscisic acid levels, and abscisic acid-deficient mutant plants are severely stunted because their ability to reduce transpiration and establish turgor is impaired. Exogenous abscisic acid treatment of mutants restores normal cell expansion and growth.

Abscisic acid is thought to initiate its effects on cells through binding to receptor proteins, although their identities and locations are still largely unknown. Activation of the putative receptor(s) causes a chain of events resulting in rapid changes in ion channels and slower changes in the pattern of gene transcription. While many individual components of this chain of events have been identified, a complete picture has not yet been obtained.

There are only few commercial formulations comprising abscisic acid in the market available which are used in agriculture for various purposes, such as improving stress tolerance of plants, slowing their growth rate, adjusting flowering phase, and other purposes. Abscisic acid has also been reported to possess insect inhibition qualities (U.S. Pat. Nos. 4,434,180 and 4,209,530 to Visscher). Abscisic acid in powdered form is currently commercially available from various Chinese suppliers like New Reyphon Biochemical Co., LTD in Jiang Xi and Lomon Biotechnology Company, Ltd., a Chinese company. Typical claims of the substance among other uses, are improving yield and quality of certain crops. Sumitomo and Valent Biosciences also offer commercial products containing abscisic acid.

One limitation associated with prior art abscisic acid formulations is abscisic acid's relatively poor solubility in unbuffered water: not more than about 3 grams per liter (about 0.3% by weight) will dissolve at ordinary temperatures. A concentration of about 3000 parts per million (ppm) is the highest concentration that can be achieved in water at room temperature. Abscisic acid solubility in hard water is even lower.

Prior art exists where the solubility of abscisic acid was enhanced by formulation of the abscisic acid as salts. For example, U.S. Pat. No. 8,278,480 B2 describes salts of S-(+)-abscisic acid and compositions containing salts of S-(+)-abscisic acid for agricultural use to improve the solubility of abscisic acid. Aqueous formulations with a loading of dissolved abscisic acid up to 10% by weight were reported. However, the salt form is considered to be less active than the uncharged, undissociated form of abscisic acid which crosses the cuticle more easily than the salt.

Another way to achieve higher load liquid formulations known in the prior art is the formulation of abscisic acid as suspension concentrate. An example is the commercial formulation BioNik from Valent Biosciences, a suspension concentrate with a concentration of S-(+)-abscisic acid of 250 g/L (25% by weight), which is used as seed treatment for delaying seed germination. Yet formulation as suspension concentrate may have disadvantages, such as slow dissolution of abscisic acid in the spray liquid and crystal growth, which may lead to clogging of nozzles. In addition, the storage stability may be limited due to sedimentation or crystal growth in the formulation. Overall, the activity of abscisic acid in solid form is inferior.

Abscisic acid has better solubility in some organic solvents, but liquid formulations of abscisic acid in many organic solvents are unacceptable because of their physicochemical properties such as flammability or volatility. Furthermore, as the organic solvent necessary for dissolution greatly exceeds the amount of active ingredient applied, the amount of suitable solvents is further limited due to potential phytotoxicity of the solvent or the possibility of contaminating food products.

Other potential solvents are of polar nature like Acetone, Ethanol, DMSO, Glycol or NMP (N-methyl-2-pyrrolidone) but limited due to solvent power, flash point, ecotoxicity or embryotoxicity.

Besides, one of the problems associated with industrial use of abscisic acid formulations is relatively poor storage stability of solvent-based abscisic acid liquid formulations, hydroxylation inactivation of 8' and 9' methyl groups in plants (U.S. Pat. No. 6,004,905) and sunlight induced degradation and isomerization of active 2-cis, 4-trans-S-(+) abscisic acid into the inactive 2-trans, 4-trans-S-(+)-abscisic acid isomer. (Kamuro Y. 1994. Plant and Chemical Regulation 29: 155-165.)

Powdered formulations of abscisic acid are most common due to the limited solubility and thus fewer stability problems as mentioned above. WO 2008/094558 A2 describes solid formulations of S-(+)-abscisic acid with improved storage stability and photochemical stability. One example of a commercial formulation is ProTone, which is a 20% by weight wettable granule formulation from Sumitomo. However, it is often more convenient to use concentrated liquid solutions instead of powders due to handling issues, dust formation and slow dissolution in the spray liquid. The dependence on variable practical factors like water pH and quality or temperature is also more pronounced. Therefore, there is a need for liquid abscisic acid formulations with high loading which are able to overcome the problems mentioned above and are better soluble in water than the acid itself.

From an economic view, maximum active substance loading levels are desirable for crop protection formulations. However, due to the low solubility of abscisic acid and the other described limitations, current commercial formulations are either solid with a maximum loading of 20% by weight or suspension concentrates where the undissolved abscisic acid is a dispersed solid in water with a maximum loading of 25% by weight. Liquid commercial formulations of dissolved abscisic acid are only known with a loading of maximum 10% by weight or less.

Different modifications of commercially important molecules, including amorphous forms and crystalline solvates, often possess different properties, which may be useful in different contexts. Thus, for example, crystalline forms are generally more stable than amorphous forms, making them useful for long-term storage of the solid material, whereas amorphous forms are often more readily soluble than crystalline forms and may thus be more useful for good bioavailability rather than crystalline forms for certain purposes.

The crystal form of a compound affects its physicochemical properties, such as melting point, solubility, or dissolution rate. It is therefore advantageous that crystal forms with a range of lattice energies, and hence a range of physico-chemical properties be available, so as to allow for example the effectiveness of treatment (e.g. agricultural (such as plant treatment), veterinary or medicinal treatment) to be optimized. Thus, for example a more stable, but less soluble form may be advantageous in some applications, whereas a higher energy, more soluble form may provide a different set of advantages in other applications.

Since abscisic acid is a biologically active agent, it is highly desirable to obtain new modification having improved solubility and/or dissolution rate.

Such new forms of abscisic acid may require lower dosage, reduced spray application rates and number of applications, as compared to crystalline and less bioactive forms. Also, the rate of formulation auxiliaries like solvents or surfactants as further chemicals besides the active ingredient ("ai") is reduced with highly active and at the same time higher loaded liquid formulations. Against diluted aqueous formulations environmental advantageous are given also by no need for biocides and lower logistic costs due to lower volumes moved.

The discovery of new modifications such as solvates of for example an agriculturally, veterinary or medicinally useful compound may provide an opportunity to improve the performance characteristics of a product. It enlarges the repertoire of materials that a formulation scientist has available for designing, for example, a dosage form of a compound with a targeted release profile or other desired characteristic. It is clearly advantageous when this repertoire is enlarged by the discovery of new solvated crystalline forms or amorphous forms of a useful compound. Solid state chemistry of a crystal cannot predict whether an organic solvent can incorporate into the crystal. The manner in which solvation of a crystal may occur is also unpredictable. There are no rules that allow prediction of whether a compound will exist as solvated form of an organic solvent. Accordingly, it will be advantageous to have new solvated crystalline forms or amorphous forms of abscisic acid, and efficient methods for their preparation.

For the reasons given above there is still a need for alternatives which permit the production of highly loaded liquid formulations with abscisic acid, where the abscisic acid is completely solubilized and retains its high biological activity.

Unexpectedly, the demand described above is met by previously unknown solvates of abscisic acid with particular N-substituted pyrrolidones, preferably N-n-butylpyrrolidone (NBP), and compositions that comprise abscisic acid in combination with the particular N-substituted pyrrolidones, preferably N-n-butylpyrrolidone (NBP).

Accordingly, the invention provides a solvate of abscisic acid with a N-substituted pyrrolidone of the formula (I), wherein R is a linear or branched, saturated alkyl group with 3 to 6 carbon atoms, more preferably 4 to 5, in particular 4 carbon atoms, wherein the N-substituted pyrrolidone of the formula (I) is preferably N-n-butylpyrrolidone ("NBP").

In addition, the invention provides a liquid high loaded up to supersaturated agrochemical composition comprising, preferably consisting of, a) 10 to 50% by weight, based on the total weight of the composition, of abscisic acid; and b) 0.1 to 90% by weight, based on the total weight of the composition, of one or more N-substituted pyrrolidones of the formula (I), wherein R is a linear or branched, saturated alkyl group with 3 to 6 carbon atoms, more preferably 4 to 5, in particular 4 carbon atoms, which is preferably N-n-butylpyrrolidone;
c) optionally up to 50% by weight, based on the total weight of the composition, of one or more co-solvents; and
d) optionally up to 50% by weight, based on the total weight of the composition, of one or more formulation auxiliaries and
e) optionally up to 50% by weight, based on the total weight of the composition, of one or more additional active ingredients.

The invention further provides a spray liquid comprising the agrochemical composition according to the invention and one or more solvents.

Another object of the invention is the use of the solvate and/or the agrochemical composition or spray liquid according to the invention for the treatment of plants. A method of regulating plant growth and/or plant development comprising the step of applying the solvate and/or agrochemical composition or spray liquid according to the invention to the plant is also provided by the invention.

The invention further discloses a method of improving stress tolerance or initiating or affecting physiological processes managing stress of a plant comprising the step of applying the solvate and/or agrochemical composition or the spray liquid according to the invention to the plant.

Moreover, a method of adjusting the flowering phase of a plant comprising the step of applying the solvate and/or agrochemical composition or the spray liquid according to the invention to the plant is also covered by the invention.

The invention further provides a method of improving the yield and quality of a crop comprising the step of applying the solvate and/or agrochemical composition or the spray liquid of the invention to the crop.

Another object of the invention is the use of the solvate as defined above for improving the stability of high load liquid abscisic acid compositions.

Moreover, the use of the solvate of the invention as defined above for promoting the interaction of abscisic acid with a plant is also disclosed herein.

The invention further provides a method of enhancing red grape coloration comprising the step of applying the solvate, the agrochemical composition or the spray liquid of the invention to the plant.

Further provided is the use of the solvate, of the agrochemical composition or the spray liquid of the invention for pre-harvest treatment of cereals to avoid pre-harvest sprouting, as well as sprouting during storage of cereal grain.

WO 2017/211572 discloses the use of N-substituted pyrrolidones to promote the penetration of agrochemically active agents, listing abscisic acid in a long list of agrochemically active agents. However, there is no hint in this document of solvates with abscisic acid and of high load liquid compositions of abscisic acid with N-substituted pyrrolidones as solvents, as well as stabilizing the active ingredient in a pseudopolymorphous state as a solvate.

The solvates of the invention advantageously permit the production of supersaturated liquid agrochemical compositions of abscisic acid, where the abscisic acid is completely solubilized and retains its high biological activity. The solvates and compositions of the invention further lead to an increase in the uptake of the active ingredient. In addition, the solvates and compositions of the invention do not exhibit phytotoxicity. They are stable and provide good dissolution properties in the spray liquid. Compositions of the invention, in particular if R in formula (I) is an alkyl group with 4 carbon atoms, such as n-butyl, further show advantageous environmental profiles.

These compositions provide the following surprising features:
Formulations with NBP are significantly more stable than otherwise identical formulations with NMP,
Precipitating abscisic acid from solutions in the solvents NMP or NBP by adding deionized water until exceeding the solubility of abscisic acid in the solvent/water mixture yields crystalline, solid precipitate with NMP, while comparable solutions with NBP show liquid amorphous phase precipitation.
After solvent evaporation of simple solutions of abscisic acid in NMP or NBP deposits are always crystalline with NMP and most frequently amorphous with NBP.

As used herein the terms "solvate of the invention", "solvate", "abscisic acid solvate", and similar terms denote that a solvent molecule is coordinated to the abscisic acid. In this case the solvent refers to the N-substituted pyrrolidone of the formula (I), in particular N-n-butylpyrrolidone (NBP). These terms and similar terms may be used interchangeably in the present invention.

The solvates of the invention preferably comprise the naturally occurring form (S)-(+)-abscisic acid. Natural abscisic acid has the following formula:

Its IUPAC name is (2Z,4E)-5-[(1S)-1-hydroxy-2,6,6-trimethyl-4-oxocyclohex-2-en-1-yl]-3-methylpenta-2,4-dienoic acid. It is commercially available, e. g. from New Reyphon Biochemical Co. Technology Co., Ltd. in Jiang Xi as well as from Sichuan Lomon Bio Technology Co., Ltd.

In addition to the natural form of abscisic acid the invention encompasses all isomers, such as the (R)-(−)-abscisic acid enantiomer, and mixtures of isomers, such as the racemic mixture of (S)-(+)- and (R)-(−)-abscisic acid. Further, the abscisic acid in the various embodiments of the invention can be generated in situ from suitable precursors, such as abscisic acid esters, e. g. abscisic acid methyl ester.

Accordingly, the solvate may be a solvate of the (S)-(+)-enantiomer, a solvate of the (R)-(−)-enantiomer, a solvate of the racemate of said enantiomers of abscisic acid, or of any mixture of said enantiomers, in particular the pseudopolymorphous state (amorphous solvate) of any of the foregoing forms of abscisic acid. The classification of solvates as a form of pseudopolymorphous state can be found e.g. in Hilfiker and von Raumer (eds, Polymorphism in the Pharmaceutical Industry, Wiley VCH, 2019 (page 2) and Polymorphism in pharmaceutical solids/edited by Harry G. Brittain. $2^{nd}$ ed. (Drugs and the pharmaceutical sciences; v. 192 (Page 1-2).

In one embodiment the solvate of the invention is an amorphous solvate.

In some embodiments, the solvate is a stoichiometric 1:1 solvate but it cannot be excluded that in liquid formulations (see below) containing also one or more formulation auxiliaries like surfactants non-stoichiometric channel types can exist also (Hilfiker and von Raumer (eds, Polymorphism in the Pharmaceutical Industry, Wiley VCH, 2019).

As used herein the term "1:1 solvate" or the similar term "monosolvate" denotes that the solvate with abscisic acid comprises approximately one solvent molecule for each molecule of abscisic acid.

In the following description, differential scanning calorimetry (DSC) parameters (e.g. desolvation peak, desolvation onset) are provided for the solvate of the invention. It should be appreciated that, unless otherwise indicated, the accuracy of the temperature values, is +/−0.1° C.

In some embodiments, the solvate is characterized by a desolvation peak at an average of approximately 125° C. (standard deviation 9° C.).

The solvate can also be characterized by thermogravimetric analysis (TGA), which measures the mass change of a sample as a function of temperature. TGA can be used to qualify weight losses observed when solvent removed from a solvate structure upon heating. The total weight loss, the onset temperature of desolvation and the shape of the weight loss curve provide information on the structure of the solvate. (Polymorphism: in the Pharmaceutical Industry, Hilfiker, R., Wiley-VHC Verlag GmbH & Co. KGaA, Weinheim, 2006 pp 77).

In some embodiments, the solvate is characterized by two peaks in the DTG-curve (Differential Thermographic Analyses) at an average turning point of approximately 180° C. (standard deviation 18° C.) and 262° C. (standard deviation 2° C.). The solvate of the invention can be prepared and isolated by a method comprising the steps of (i) dissolving abscisic acid in an N-substituted pyrrolidone of formula (I), preferably N-n-butylpyrrolidone; and (ii) evaporating the N-substituted pyrrolidone of formula (I), preferably N-n-butylpyrrolidone.

In this method conditions for the evaporation must be chosen that avoid decomposition of the solvate of the invention, as shown e. g. in the working examples. In one embodiment, the excess solvent is evaporated until constant weight at room temperature.

A further method for preparing and isolating a solvate of abscisic acid with an N-substituted pyrrolidone of formula (I), preferably N-n-butylpyrrolidone, comprises the steps of (i) dissolving abscisic acid in an N-substituted pyrrolidone of formula (I), preferably N-n-butylpyrrolidone; (ii) providing conditions suitable for precipitating the abscisic acid solvate; and (iii) isolating the precipitated solvate.

A further method for preparing a solvate of abscisic acid with an N-substituted pyrrolidone of formula (I), preferably N-n-butylpyrrolidone, an agrochemical composition of the invention (as described below) or a spray liquid of the invention (as described below) comprises the steps of (i) dissolving a precursor molecule of abscisic acid, such as an abscisic acid ester, e. g. abscisic acid methyl ester, in an N-substituted pyrrolidone of formula (I), preferably N-n-butylpyrrolidone; and (ii) generating abscisic acid in situ from the precursor molecule.

The solvates of the invention are suitable for producing high load compositions of abscisic acid.

The agrochemical composition according to the invention comprises
a) 10 to 50% by weight, preferably 15 to 40% by weight, more preferably 25 to 35% by weight, based on the total weight of the composition, of abscisic acid; and
b) 0.1 to 90% by weight, preferably 10 to 85% by weight, more preferably 25 to 75% by weight, based on the total weight of the composition, of one or more N-substituted pyrrolidones of the formula (I), wherein R is a linear or branched, saturated alkyl group with 3 to 6, more preferably 4 to 5, in particular 4 carbon atoms, in a particularly preferred embodiment, the N-substituted pyrrolidone is N-n-butylpyrrolidone.
c) optionally up to 50% by weight, preferably 0 or 0.1 to 30% by weight, more preferably 0 or 1% to 20% by weight, based on the total weight of the composition, of one or more co-solvents; and
d) optionally up to 50% by weight, preferably 0.1 to 40% by weight, more preferably 1% to 35% by weight, based on the total weight of the composition, of one or more formulation auxiliaries and
e) optionally up to 50% by weight, preferably 0 or 0.1 to 40% by weight, more preferably 0 or 1% to 30% by weight, based on the total weight of the composition of one or more additional active ingredients, including other derivatives of abscisic acid like glucose esters or the o-glucoside.

The compositions of the present invention preferably comprise the naturally occurring form (S)-(+)-abscisic acid. For use in a commercial agricultural product the naturally occurring form of abscisic acid is preferable due to substantially enhanced bioactivity.

In addition to the natural form of abscisic acid the composition invention may comprise all isomers, such as the (R)-(−)-abscisic acid enantiomer, and mixtures of isomers, such as the racemic mixture of (S)-(+)- and (R)-(−)-abscisic acid as well as polymorphous states, amorphous states and pseudopolymorphous states (solvate) of abcsicic acid with N-substituted pyrrolidones of the formula (I), in particular N-butylpyrrolidone.

Preferably, in the compositions of the invention abscisic acid (in any of the isomeric forms described above) is present as a solvate of the invention. This also applies to all preferred embodiments of the compositions of the invention and application forms, such as spray liquids.

In one preferred embodiment the composition of the invention comprises no (0%) co-solvent (c).

In a further preferred embodiment, the composition of the invention comprises at least 0.1% by weight of one or more co-solvents (c).

The co-solvent—if present—is preferably selected from the group consisting of aliphatic or aromatic hydrocarbons, such as mineral oils, toluene, xylenes or naphthalene derivatives; halogenated aliphatic or aromatic hydrocarbons such as methylene chloride or chlorobenzene, oils, plant-based oils such as corn germ oil or rapeseed oil; oil derivatives such as rapeseed oil methyl ester; di- or trihydric alcohols, such as ethylene glycol, diethylene glycol, propylene glycol and glycerol; polyglycols, such as polyethylene glycols, polypropylene glycols and/or mixed polyalkylene glycols (PAGs); polar ethers such as tetrahydrofuran (THF) or dioxane; alkylene glycol monoalkyl and dialkyl ethers such as, propylene glycol monomethyl ether, propylene glycol monoethyl ether, ethylene glycol monomethyl ether or monoethyl ether; diglyme or tetraglyme; amides such as dimethylformamide (DMF), dimethylacetamide, dimethylcaprylamide, dimethylcapramide (®Hallcomide); ketones such as acetone; esters based on glycerol and carboxylic acids, such as glycerol mono-, di- or triacetate; lactams; lactate esters having chain lengths of 1 to 10 carbon atoms in the ester moiety; carbonic diesters; nitriles such as acetonitrile, propionitrile, butyronitrile, or benzonitrile; sulfoxides and sulfones such as dimethyl sulfoxide (DMSO) and sulfolane. More preferably, the co-solvent is selected from amides, preferably N,N-dialkylamides, more preferably N,N-dimethylamides of carboxylic acids having 5 to 20, preferably 6 to 15, more preferably 8 to 12 carbon atoms. Most preferably, the co-solvent is nonanoyl dimethyl amide.

In a preferred embodiment, the composition of the invention comprises at least 0.1% by weight of one or more formulation auxiliaries (d).

In a further preferred embodiment the composition of the invention comprises no (0%) formulation auxiliary (d).

The formulation auxiliaries (d) used may be those substances which are suitable for imparting particular properties, such as particular physical, technical and/or biological properties, to the compositions of the invention or to the use forms prepared from these compositions (for example ready-to-use crop protection agents such as spray liquids or seed dressing products). In general, the compositions of the invention or respective spray liquids can contain any solid or liquid formulation auxiliary which is commonly used for formulation purposes.

The formulation auxiliaries (d) are preferably selected from the group consisting of acidifiers, adjuvants, dispersing agents, emulsifiers, photodegradation stabilizer, spontaneity agents and wetting agents. More preferably, the formulation auxiliaries are selected from the group consisting of at least one dispersing agent and/or wetting agent and/or acidifier. Most preferably, the agrochemical composition comprises at least one dispersing agent, at least one wetting agent and at least one acidifier, wherein the dispersing agent, wetting agent and acidifier may be the same compound or different compounds.

Dispersing agents are defined as chemical additives to cause an even distribution of liquid and solid ingredients throughout the agrochemical composition. An even distribution can be achieved by dispersing as well as emulsifying the liquid or solid ingredients which also include the term emulsifier.

Examples of dispersing agents and wetting agents are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkyl sulfonates, alkyl sulfates, arylsulfonates, protein hydrolyzates, lignosulfite waste liquids and methyl cellulose.

Examples of acidifiers are inorganic and organic acids with a pH value lower than that of abscisic acid. Preferably, acidifiers are carboxylic acids with 1 to 15 carbon atoms, more preferably with 1 to 8 carbon atoms, most preferably 2 to 6 carbon atoms. Propionic acid and lactic acid are particularly preferred acidifiers.

Preferred examples of adjuvants are e. g. example. spreaders, for example alkylsiloxanes, and/or salts, for example organic or inorganic ammonium or phosphonium salts, for example ammonium sulfate or diammonium hydrogenphosphate, and/or retention promoters and/or humectants, for example glycerol and/or penetrants and/or stickers (agents which promote sticking to the plant surface), such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids, and/or functional polymers.

Useful penetrants in the present context are all those substances which are typically used to improve the penetration of agrochemical actives into plants.

Penetrants are defined in this context by their ability to penetrate from the (generally aqueous) application liquid and/or from the spray deposit into the cuticle of the plant and hence increase the mobility of active ingredients in the cuticle. The method described in the literature (Baur et al., 1997, Pesticide Science 51, 131-152) can be used to determine this property. Examples include alcohol alkoxylates, for example coconut fat ethoxylate (10) or isotridecyl ethoxylate (12), fatty acid alkyl esters, for example rapeseed oil methyl ester or soya oil methyl ester, fatty amine alkoxylates, for example tallowamine ethoxylate (15) or ammonium salts phosphonium salts, for example ammonium sulfate or diammonium hydrogenphosphate, vegetable oils, for example rapeseed oil, sunflower oil, or mineral oils, for example paraffin oils.

Useful retention promoters include all those substances which reduce dynamic surface tension, for example dioctyl sulfosuccinate, or increase viscoelasticity, for example hydroxypropylguar polymers.

Useful functional polymers, which may be present in the compositions according to the invention, are high molecular weight compounds of synthetic or natural origin having a molar mass of greater than 10 000. The functional polymers may act, for example, as an anti-drift agent or increase rain resistance.

Further possible formulation auxiliaries include spontaneity promoters. The presence of spontaneity promoters, like branched alcohol ethoxylates or butylalkcoxylates or related surfactants, is advantageous when an active ingredient and/or further formulation auxiliary is insoluble in water and when application is executed in water.

Additional components may be stabilizers, such as cold stabilizers (antifreezes), preservatives, antioxidants, light stabilizers, or other agents which improve chemical and/or physical stability. Foam generators or defoamers may additionally be present.

Preservatives used may be organic acids and esters thereof, for example ascorbic acid, ascorbyl palmitate, sorbate, benzoic acid, methyl and propyl 4-hydroxybenzoate, propionates, phenol, for example 2-phenylphenate, 1,2-benzisothiazolin-3-one, formaldehyde, sulfurous acid and salts thereof.

Suitable defoamers are fatty acid alkyl ester alkoxylates, organopolysiloxanes such as polydimethylsiloxanes and mixtures thereof with microfine, optionally silanized silica; perfluoroalkylphosphonates and -phosphinates, paraffins, waxes and microcrystalline waxes, and mixtures thereof with silanized silica. Also advantageous are mixtures of various foam inhibitors, for example those of silicone oil, paraffin oil and/or waxes.

In addition, the compositions and the use forms derived therefrom optionally comprise, as formulation auxiliaries fragrances, protective colloids, binders, adhesives, thickeners, thixotropic agents, sequestrants and/or complexing agents. Further possible formulation auxiliaries are mineral and vegetable oils.

In one preferred embodiment the composition of the invention comprises no (0%) additional active ingredient (e).

In a further preferred embodiment, the composition of the invention comprises at least 0.1% by weight of one or more additional active ingredients (e).

The additional active ingredients (e)—if present—are different from abscisic acid and are preferably agrochemical active ingredients including other derivatives of abscisic acid preferably glucose esters or the o-glucoside.

They are preferably selected from the group consisting of pesticides, plant growth regulators, plant nutrients, repellents, safeners and combinations of two or more of these active ingredients.

Examples of herbicides and plant growth regulators include:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminocyclopyrachlor-potassium, aminocyclopyrachlor-methyl, aminopyralid, amitrole, ammonium sulfamate, ancymidol, anilofos, asulam, atrazine, aviglycine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, benzyladenine, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbaryl, carbetamide, carfentrazone, carfentrazone-ethyl, carvone, chlorocholine chloride, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, 4-chlorophenoxyacetic acid, chlorophthalim, chlorpropham, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cloxyfonac, cumyluron, cyanamide, cyanazine, cyclanilide, cycloate, cyclosulfamuron, cycloxydim, cycluron, cyhalofop, cyhalofop-butyl, cyperquat, cyprazine, cyprazole, cytokinine, 2,4-D, 2,4-DB, daimuron/dymron, dalapon, daminozide, dazomet, n-decanol, desmedipham, desmetryn, detosyl-pyrazolate (DTP), diallate, diaminozide, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, diisopropylnaphthalene, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethyl naphthylacetate, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl] ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprim idol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)phenyl]-2-methylpentanamide, NGGC-011, 1-naphthylacetic acid (NAA), naphthylacetamide (NAAm), 2-naphthoxyacetic acid, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitroguaiacolate, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxam id, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, tribufos, trichloroacetic acid (TCA), triclopyr, tridiphane, trietazine, trifloxysulfuron, trifloxysulfuron-sodium, trifluralin, triflusulfuron, triflusulfuron-methyl, trimeturon, tritosulfuron, tsitodef, vernolate, ZJ-0862, i.e. 3,4-dichloro-N-{2-[(4,6-dimethoxypyrimidin-2-yl)oxy]benzyl}aniline, and the following compounds: Plant growth regulators are preferably phytohormones that control physiological reactions, such as growth, flowering rhythm, cell division and seed ripening. Examples of plant growth regulators include natural and synthetic plant hormones such as benzyladenine, caprylic acid, decanol, indoleacetic acid, jasmonic acid and esters thereof, salicylic acid and esters thereof, trinexapac and esters of it, such as trinexapac-ethyl, uniconazole, uniconazole-P, gibberellic acid, triacontanol, kinetin and brassinosteroids. Further preferred are derivatives of abscisic acid in particular glucose esters as well as the o-glucoside of abscisic acid.

Examples of fungicides include:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexam id, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl] 1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam (mixture of the syn-epimeric racemate 1RS,4SR,9RS and of the anti-epimeric racemate 1RS,4SR,9SR), isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]

oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulfur and sulfur preparations, for example calcium polysulfide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) Inhibitors of ATP production, for example fentin acetate, fentin chloride, fentin hydroxide and silthiofam.

(9) Cell wall synthesis inhibitors, for example benthiavalicarb, dimethomorph, flumorph, iprovalicarb, mandipropam id, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulfate, diphenylamine, ecomat, fenpyrazamine, flumetover, fluoromide, flusulfamide, flutianil, fosetyl-aluminum, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1 S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl] pyridine-3-carboxamide, (5-bromo-2-methoxy-4-methylpyridin-3-yl)(2,3,4-trimethoxy-6-methylphenyl) methanone, N-[2-(4-{[3-(4-chlorophenyl)prop-2-yn-1-yl]oxy}-3-methoxyphenyl)ethyl]-N2-(methylsulfonyl) valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

Examples of bactericides include the following:
bronopol, dichlorophen, nitrapyrin, nickel dimethyldithiocarbamate, kasugamycin, octhilinon, furancarboxylic acid, oxytetracycline, probenazole, streptomycin, tecloftalam, copper sulfate and other copper preparations.

Examples of insecticides, acaricides and nematicides include the following:

(1) Acetylcholinesterase (AChE) inhibitors, such as carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan; or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin; or DDT; or methoxychlor.
(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam; or nicotine.
(5) Allosteric activators of the nicotinergic acetylcholine receptor (nAChR), for example spinosyns, e.g. spinetoram and spinosad.
(6) Chloride channel activators, for example avermectins/milbemycins, e.g. abamectin, emamectin benzoate, lepimectin and milbemectin.
(7) Juvenile hormone imitators, for example juvenile hormone analogs e.g. hydroprene, kinoprene and methoprene; or fenoxycarb; or pyriproxyfen.
(8) Active ingredients with unknown or nonspecific mechanisms of action, for example alkyl halides, e.g. methyl bromide and other alkyl halides; or chloropicrin; or sulfuryl fluoride; or borax; or tartar emetic.
(9) Selective antifeedants, for example pymetrozine; or flonicamid.
(10) Mite growth inhibitors, for example clofentezine, hexythiazox and1 diflovidazin; or etoxazole.
(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron; or organotin compounds, e.g. azocyclotin, cyhexatin and fenbutatin oxide; or propargite; or tetradifon.
(13) Oxidative phosphorylation decouplers that interrupt the H proton gradient, for example chlorfenapyr, DNOC and sulfluramid.
(14) Nicotinergic acetylcholine receptor antagonists, for example bensultap, cartap hydrochloride, thiocyclam, and thiosultap-sodium.
(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Molting disruptors, dipteran, for example cyromazine.
(18) Ecdysone receptor agonists, for example chromafenozide, halofenozide, methoxyfenozide and tebufenozide.
(19) Octopaminergic agonists, for example amitraz.
(20) Complex-III electron transport inhibitors, for example hydramethylnon; or acequinocyl; or fluacrypyrim.
(21) Complex-I electron transport inhibitors, for example METI acaricides, e.g. fenazaquin, fenpyroximate, pyrimidifen, pyridaben, tebufenpyrad and tolfenpyrad; or rotenone (Derris).
(22) Voltage-dependent sodium channel blockers, for example indoxacarb; or metaflumizone.
(23) Inhibitors of acetyl-CoA carboxylase, for example tetronic and tetramic acid derivatives, e.g. spirodiclofen, spiromesifen and spirotetramat.
(24) Complex-IV electron transport inhibitors, for example phosphines, e.g. aluminum phosphide, calcium phosphide, phosphine and zinc phosphide; or cyanide.
(25) Complex-II electron transport inhibitors, for example cyenopyrafen.
(26) Ryanodine receptor effectors, for example diamides, e.g. chlorantraniliprole and flubendiamide.

Further active ingredients with an unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidaclothiz, iprodione, pyridalyl, pyrifluquinazon and iodomethane; and additionally preparations based on *Bacillus firmus* (1-1582, BioNeem, Votivo).

Biological control agents are known to those skilled in the art and are described, for example, in "The Manual of Biocontrol Agents, 5th edition, editor: Dr. Roma Gwynn, BCPC 2014".

Examples of repellents include diethyltolylamide, ethylhexanediol and butopyronoxyl.

Examples of plant nutrients include customary inorganic or organic fertilizers for supplying plants with macro- and/or micronutrients, for example ammonium-, potassium- or phosphorus-containing fertilizers.

In one embodiment the composition of the invention comprises no (0%) further formulation auxiliary (d) or additional active ingredient (e).

In further preferred embodiment the composition of the invention comprises at least 0.1% by weight of one or more formulation auxiliaries (d) and/or one or more additional active ingredients (e).

In further preferred embodiment the composition of the invention comprises at least 0.1% by weight of one or more formulation auxiliaries (d) and no additional active ingredients (e).

In further preferred embodiment the composition of the invention comprises at least 0.1% by weight of one or more formulation auxiliaries (d) and one or more additional active ingredients (e).

In further embodiment the composition of the invention comprises at least 0.1% by weight of one or more additional active ingredients (e) and no formulation auxiliaries (d).

The compositions of the invention can be prepared by customary methods known to those skilled in the art, such as mixing of components a), b), optionally c), d) and optionally e).

The spray liquid according to the invention comprises the agrochemical composition described above and one or more solvents, preferably water. It is preferably prepared from the composition of the invention, preferably by diluting the composition of the invention with the one or more solvents.

Preferably the spray liquid comprises 0.001 to 20% by weight, more preferably 0.002 to 1% by weight, most preferably 0.005 to 0.2% by weight of the agrochemical composition described above, based on the weight of the spray liquid.

In a preferred embodiment, the spray liquid comprises
a) 0.0001 to 10% by weight, preferably 0.0002 to 0.5% by weight, most preferably 0.0005 to 0.1% by weight of abscisic acid, preferably (S)-(+)-abscisic acid; most preferable the solvate of (S)-(+)-abscisic acid with N-butylpyrrolidon.

b) 0.0001 to 10% by weight, preferred 0.0002% to 1.1% by weight, most preferred 0.0005% to 0.2% by weight of one or more N-substituted pyrrolidones of the formula (I) defined above;

c) optionally up to 10% by weight, preferably 0.0001 to 1% by weight, more preferably 0.001 to 0.1% by weight of one or more co-solvents; and d) optionally up to 10% by weight, preferably 0.0001 to 1% by weight, more preferably 0.001 to 0.1% by weight of one or more formulation auxiliaries and e) optionally up to 10% by weight, preferably 0.0001 to 1% by weight, more preferably 0.001 to 0.1% by weight of one or more additional active ingredients.

In a preferred embodiment of the invention the spray liquid of the invention consists of a) to e) and the solvent, i.e. the percentage values of components a) to e) and of the solvent add up to 100%.

The agrochemical composition of the invention and the spray liquid of the invention may be used for the treatment of plants in any phase of their development. Exemplary plants that may be advantageously treated by the agrochemical composition or the spray liquid of the invention may be cereals including wheat and, rice, the C4 plants corn, sugar cane and sorghum, tobacco, coffee, cotton, grape, citrus fruits, apple, tomatoes, peanuts. Fruits of all climacteric fruits like apple and other pome fruits, peach and other stone fruits, avocado, banana, figs, mango, papaya, tomato and vegetables like cabbage, allium spec., pepper, eggplant, cucumber and other cucurbitaceae, asparagus, soybean and others. Another use is to correct greening effects of fungicides of e.g. the strobilurin group or carboxamides in order to facilitate ripening.

Furthermore, the agrochemical composition or the spray liquid of the invention may be used for example for regulating plant growth and/or plant development, improving stress tolerance of plants or initiating or affecting physiological processes managing stress of a plant, adjusting the flowering phase of plants and improving the yield and quality attributes like content of assimilates or color of crops.

The agrochemical composition of the invention and the spray liquid of the invention may also be used for the treatment of seeds to postpone seed germination and avoid unfavorable germination of corn, soybean, sorghum, sugarcane, canola, and spring cereals like barley, wheat and rye.

Moreover, the solvate of the invention can be used for promoting the interaction of abscisic acid with a plant.

The invention is further illustrated but not limited by the following examples.

EXAMPLES

The percentages stated hereinafter are percent by weight (% by weight), unless explicitly stated otherwise.

The raw materials used are:

| | |
|---|---|
| Abscisic acid | (S)-(+)-abscisic acid (purity 90% by weight), JiangXi New Reyphon Biochemical Co., LTD |
| Genagen NBP | N-butyl pyrrolidone solvent, Clariant |
| Genagen PA | Nonanoyl dimethyl amide solvent, Clariant |
| Emulsogen EL 360 | Castor oil ethoxylate dispersing agent/emulsifier, Clariant |
| Tivogen DR3401 | Polyglycerinester with 20% NBP dispersing agent/emulsifier, Clariant |
| Synergen 848 | n-butyl EO/PO co-polymer emulsifier/wetting agent, Clariant |
| mPEG ester | Fatty acid mPEG ester/wetting agent, Clariant |
| Propionic acid | Propionic acid acidifier, Sigma Aldrich |
| Emulsogen MTP030 | Vegetable fatty alcohol alkoxylate, emulsifier/dispersing agent/adjuvant, Clariant |
| Synergen KN | Adjuvant blend, adjuvant, Clariant |
| LMF 1002 | 农宝 S-ABA 0.1% SL commercial Formulation Sichuan Lomon Bio Technology CO. LTD |
| LMF 1009 | 福施灌 S-ABA 10% commercial Formulation Sichuan Lomon Bio Technology CO. LTD |

Example 1: Physical State of the Abscisic Acid in Correlation with the Solvent

In this test, the modification of physical state of the abscisic acid in correlation with the solvent was observed in the microscope with and without polarized light (POLAM).

The following solutions 1) to 6) are prepared:

Solution 1: 5% Abscisic acid in N-butylpyrrolidone

Solution 2: 5% Abscisic acid in N-methylpyrrolidone

Solution 3: 5% Abscisic acid in N-butylpyrrolidone/deionised water (9:1)

Solution 4: 5% Abscisic acid in N-methylpyrrolidone/deionised water (9:1)

Solution 5: 5% Abscisic acid in N-butylpyrrolidone/tap water (9:1)

Solution 6: 5% Abscisic acid in N-methylpyrrolidone/tap water (9:1)

In each case 1 μl of the solutions described above 1) to 6) where applied on silanized glass. The solutions were allowed to stand on the slides at a room temperature of approx. 25° C. and 20-50% relative humidity for 24 hours were a drying took place. The slides were examined and pictures were taken of the original edge A) and center of the droplet B) at magnification 400×, with and without a polarized light filter. The results are shown in FIG. 1 (NMP) and FIG. 2 (NBP).

It was found that the active compound abscisic acid from the solutions containing N-methylpyrrolidone (solution 2) 4) 6)) was crystallized (see FIG. 1) and no longer present in an available form for uptake out of the spray deposit in contrast to the solutions containing N-butylpyrrolidone (solution 1) 3) 5)) were the active compound abscisic acid is still present in a solvated form (see FIG. 2). This solvate of the active compound abscisic acid helps to improve the solubilization as well as the availability of those active ingredients in the spray deposit for uptake into the plant.

Example 2: Preparation of High Loaded Abscisic Acid Formulations

The abscisic acid formulations A1 to A7 displayed in Table 1 were produced by mixing the various components. The preparations are then stored for eight weeks at −10° C., 40° C., 25° C. (room temperature) and for two weeks at 54° C. in order to determine the storage stability and the phase behavior.

TABLE 1

Abscisic acid formulations (numbers are % by weight based on formulation)

| | A1 | A2 Non inventive example | A3 | A4 Non inventive example | A5 | A6 Non inventive example | A7 |
|---|---|---|---|---|---|---|---|
| (S)-Abscisic acid (ABA) 90% by weight | 40.00 | 40.00 | 30.00 | 30.00 | 30.00 | 30.00 | 30.00 |
| Genagen NBP | 60.00 | | 39.00 | | 30.00 | | 27.50 |
| NMP | | 60.00 | | 39.00 | | 30.00 | |
| Genagen PA | | | | | | | 10.00 |
| Tivogen DR3401 | | | 5.00 | 5.00 | 5.00 | 5.00 | 5.00 |
| Emulsogen EL 360 | | | 15.00 | 15.00 | 2.50 | 2.50 | 2.50 |
| Synergen 848 | | | 5.00 | 5.00 | 5.00 | 5.00 | 5.00 |
| Emulsogen MTP 030 | | | | | 6.00 | 6.00 | |
| Propionic acid | | | | | 4.00 | 4.00 | 3.00 |
| mPEG ester | | | | | 17.50 | 17.50 | 17.00 |
| Synergen KN | | | 6.00 | 6.00 | | | |
| Total | | | 100.00 | 100.00 | 100.00 | 100.00 | 100.00 |
| Appearance | Clear liquid | Clear liquid | Clear liquid | Unstable suspension | Clear liquid | Unstable suspension, ai not soluble | Clear liquid |
| Storage stability 8 weeks −10/ 40/25° C. | OK | 40° C. and 25° C. OK; at −10° C. crystallization | OK | — | OK | — | OK |
| 2 weeks 54° C. | OK | OK | OK | — | OK | — | OK |

Comparison of the formulations A3 versus A4 and A5 versus A6 shows that the formulations with NBP are significantly more stable than otherwise identical formulations with NMP.

Example 3: Penetration Enhancement

In this test, the penetration of abscisic acid through enzymatically isolated cuticles of pear tree leaves was measured. The principle of the method has been published and described in detail e.g. in WO-A-2005/194844 or WO2017211572 A1.

To determine the penetration, 10 μl a spray liquor of the composition mentioned in the examples were applied to the outer side of a cuticle. In the spray liquors tap water was used in each case.

After application of the spray liquors was allowed to evaporate in each case the water, then in each case the chambers were inverted and placed in thermostated troughs, with air being blown at a defined temperature and humidity to the outside of the cuticle. The incipient penetration therefore took place at a relative humidity of 56% and a set temperature at 10° C. and 25° C. The penetration of active ingredients was determined by High Performance Liquid Chromatography (HPLC).

The table shows that the uptake of the active ingredient from the abscisic acid formulations of the invention is strongly increased compared to the ai on its own and increased compared to the tested commercial benchmark formulations. As uptake through cuticular penetration is important for biological activity, we expect excellent performance of the inventive compositions in the field.

TABLE 2

Penetration of abscisic acid (active ingredient concentration 0.1 g/L in spray liquid) in the presence of test substances

| | Mean penetration for abscisic acid (amount of active ingredient 0.1 g/L) after time (n = 8-10) in % | | | |
|---|---|---|---|---|
| | 25° C./56% rH | | 10° C./56% rH | |
| Test substance | 1 day | 2 day | 1 day | 2 day |
| Control (pure active ingredient) | 1.4 | 2.2 | 5.3 | 8.2 |
| Composition A3 | 5.3 | 11.4 | 9.9 | 10.6 |
| Composition A4 | 2.4 | 4.4 | 11.0 | 13.6 |
| Composition A5 | 7.0 | 14.5 | 11.3 | 11.6 |
| Composition A6 | Not measurable | Not measurable | Not measurable | Not measurable |
| Commercial LMF 1002 (ABA SL 0.1%) | 5.3 | 8.7 | 12.1 | 13.3 |
| Commercial LMF 1009 (ABA SP 10%) | 1.6 | 2.8 | — | — | rH = air humidity

Example 4: Phytotoxicity

The plant compatibility of the abscisic acid was checked using indicator plants such as poinsettia plants, e.g. the Merlot variety. If no necrosis or other phytotoxicity symptoms such as leaf curl-up or deformation in any case were observed the substance is considered plant compatible and not phytotoxic.

The compositions of the invention did not show phytotoxicity symptoms at relevant use concentrations of 0.1 g/Lai. The tested reference substance (ethoxylated lauryl alcohol at 1 g/L) caused strong distinct necrosis within one day.

Example 5: Differential Scanning Calorimetry (DSC)

In order to determine differences in the crystallographic form of the abscisic acid a DSC was conducted out of the deposit of A) 40% abscisic acid in N-butylpyrrolidone solution; B) 40% abscisic acid in N-methylpyrrolidone solution C) active ingredient of abscisic acid (90% purity).

For the deposit the 40% abscisic acid solution was dried until weight constancy. Afterwards the samples were used in the test sorptions isotherme. As there were no changes in weight from 3-30% rh, these samples were used for the DSC Measurement compared to abscisic acid active (New Reyphon 90%/also taken from the sorption isotherme experiment).

TABLE 3

Differential Scanning Calorimetry (DSC)
Desolvation onset and peak of heating phase one and two

|   |   | 1. heating phase | | 2. heating phase | | |
|---|---|---|---|---|---|---|
|   |   | desolvation onset [° C.] | desolvation peak [° C.] | desolvation onset [° C.] | desolvation peak [° C.] | glas point [° C.] |
| A | average | 52.67 | 107.74 | 103.46 | 125.62 | 7.74 |
|   | St. dev. | 42.58 | 19.71 | 9.47 | 9.04 | 0.79 |
| B | average | 142.99 | 149.64 | 141.06 | 150.86 | 28.74 |
|   | St. dev. | 5.39 | 4.69 | 1.79 | 1.44 | 0.61 |
| C | average | 157.86 | 161.11 | 149.98 | 157.34 | 35.77 |
|   | St. dev. | 0.48 | 0.23 | 0.62 | 0.20 | 0.51 |

In addition a TGA was conducted with the same samples.

Example 6: Thermogravimetric Analysis (TGA)

After long term drying and evaporation of deposits of abscisic acid in NMP and NBP striking analytical differences have been observed in the TGA.

Deposits of abscisic acid in NBP show two distinct peaks in the DTG-curve whereas deposits of abscisic acid show only one peak at approx. 268° C. Deposits of abscisic acid in NMP show occasionally a small second peak in front of the peak at approx. 262° C.-268° C., which is visible in all three measurements.

TABLE 4

TGA data characterizing by the TG curve

|   |   | Peak1 | | | Peak 2 | | |
|---|---|---|---|---|---|---|---|
|   |   | phase [%] | turning point [° C.] | average [° C.] | phase [%] | turning point [° C.] | average [° C.] |
| A | average | 32.62 | 180.45 | 166.82 | 66.89 | 262.61 | 256.37 |
|   | St. dev. | 14.28 | 18.14 | 6.16 | 14.07 | 2.09 | 4.82 |
| B | average | 4.28 | 149.84 | 136.67 | 98.20 | 263.17 | 255.42 |
|   | St. dev. | 2.05 | 0.23 | 2.02 | 2.68 | 6.95 | 3.22 |
| C | average |   |   |   | 99.67 | 268.50 | 261.66 |
|   | St. dev. |   |   |   | 0.45 | 5.37 | 2.29 |
| NBP | '4-1 | 1.02 | 172 | 152.04 |   |   |   |

Example 7: Precipitation in an Aqueous Solution

To precipitate the solvate in an aqueous solution samples were prepared by mixing A) solutions of 40% abscisic acid in N-butylpyrrolidone and B) 40% abscisic acid in N-methylpyrrolidone in deionized water at a ratio of 1:1 and 1:2. To separate the precipitation samples were centrifugated for a short time (min).

Striking differences were observed between the samples. Whereas the samples prepared in the 40% abscisic acid in N-methylpyrrolidone solution were strongly crystallizing, the samples with the 40% abscisic acid in N-butylpyrrolidone solution formed two liquid phases which even stay stable when cooling the aqueous solution down to 5° C. as well as trying to inoculate in order to provoke a crystallization.

The invention claimed is:

1. A solvate of abscisic acid with a N-substituted pyrrolidone of the formula (I)

wherein R is a linear or branched, saturated alkyl group with 3 to 6 carbon atoms.

2. The solvate according to claim 1, wherein the solvate is in an amorphous state.

3. The solvate according to claim 1, wherein the abscisic acid is the naturally occurring form (S)-(+)-abscisic acid.

4. An agrochemical composition comprising the solvate according to claim 1.

5. A spray liquid formulation comprising the solvate according to claim 1.

6. The spray liquid formulation according to claim 5, further comprising one or more solvents selected from water, glycerin, a vegetable oil-based liquid carrier, and combinations of these.

7. A method of treating a plant, the method comprising contacting the plant with a composition comprising the solvate according to claim 1.

8. A method for preparing the solvate according to claim 1, the method comprising the steps of (i) dissolving a precursor molecule of abscisic acid in an N-substituted pyrrolidone of formula (I); and (ii) generating abscisic acid in situ from the precursor molecule.

9. The solvate according to claim 1, wherein the abscisic acid and the N-substituted pyrrolidone of the formula (I) are present in a stoichiometric ratio of 1:1.

10. The solvate according to claim 1, wherein the N-substituted pyrrolidone of the formula (I) is N-n-butylpyrrolidone.

11. The solvate according to claim 10, wherein the abscisic acid is (S)-(+)-abscisic acid.

12. The solvate according to claim 10, wherein the solvate is characterized by a desolvation peak at an average of approximately 125° C., as determined by differential scanning calorimetry.

13. The solvate according to claim 10, wherein the solvate is characterized by two peaks in a differential thermographic analyses curve at an average turning point of approximately 180° C. and 262° C.

14. The agrochemical composition according to claim 4, wherein the composition comprises
 a) 10 to 50% by weight, based on the total weight of the composition, of abscisic acid; and
 b) 0.1 to 90% by weight, based on the total weight of the composition, of one or more N-substituted pyrrolidones of the formula (I).

15. The agrochemical composition according to claim 14, wherein the composition comprises 10 to 40 wt % of a) and 10 to 90 wt % of b).

16. The agrochemical composition according to claim 14, wherein the composition further comprises
 c) 0 to 50% by weight, based on the total weight of the composition, of one or more co-solvents;
 d) 0 to 50% by weight, based on the total weight of the composition, of one or more formulation auxiliaries; and
 e) 0 to 50% by weight, based on the total weight of the composition, of one or more additional active ingredients.

17. The agrochemical composition according to claim 14, wherein the composition comprises 10 to 50 wt % of a), 0.1 to 85 wt % of b), and at least 0.1 wt % of one or more of c), d), and e).

18. The agrochemical composition according to claim 17, wherein the composition comprises from 0.1 to 30 wt % of c), from 0.1 to 40 wt % of d), and from 0.1 to 40 wt % of e).

19. The agrochemical composition according to claim 16, wherein the one or more formulation auxiliaries is selected from the group consisting of acidifiers, adjuvants, dispersing agents, emulsifiers, photodegradation stabilizer, spontaneity agents, and wetting agents.

* * * * *